(12) United States Patent
Maitra et al.

(10) Patent No.: US 6,322,817 B1
(45) Date of Patent: Nov. 27, 2001

(54) FORMULATIONS OF PACLITAXEL, ITS DERIVATIVES OR ITS ANALOGS ENTRAPPED INTO NANOPARTICLES OF POLYMERIC MICELLES, PROCESS FOR PREPARING SAME AND THE USE THEREOF

(75) Inventors: Amarnath Maitra; Sanjeeb Kumar Sahoo, both of Delhi; Prasanta Kumar Ghosh, New Delhi; Anand C. Burman, Ghaziabad; Rama Mukherjee, Ghaziabad; Dhiraj Khattar, Ghaziabad; Mukesh Kumar, Ghaziabad; Soumendu Paul, Ghaziabad, all of (IN)

(73) Assignees: Dabur Research Foundation; Delhi University, both of (IN)

( * ) Notice: Subject to any disclaimer, the term of this patent is extended or adjusted under 35 U.S.C. 154(b) by 0 days.

(21) Appl. No.: 09/401,927

(22) Filed: Sep. 23, 1999

(30) Foreign Application Priority Data

Feb. 17, 1999 (IN) ................................. 263/DEL/99

(51) Int. Cl.⁷ ............................ A61K 47/30; A61K 9/14; A61K 9/50
(52) U.S. Cl. ....................... 424/489; 424/486; 424/487; 424/501; 514/772.3
(58) Field of Search .................................... 424/489, 486, 424/487, 501; 549/510, 511; 514/772.3

(56) References Cited

U.S. PATENT DOCUMENTS

| 5,648,090 | 7/1997 | Rahman et al. | 424/450 |
| 5,648,506 | * 7/1997 | Desai et al. | 549/510 |
| 5,684,169 | 11/1997 | Hamada et al. | 549/510 |

OTHER PUBLICATIONS

Kwon et al., "Polymeric Micelles as New Drug Carriers" Advanced Drug Delivery Rev., vol. 21 pp. 107–116 (1996).*
Kwon, G.S. et al." Polymeric Micelles as New Drug Carriers" *Advanced Drug Delivery Rev.*, vol. 21 (1996) pp. 107–116.
Kwon, G.S. et al. "Block Copolymer Micelles as Long–Circulating Drug Vehicles" *Advanced Drug Delivery Rev.* vol. 16 (1995) pp. 295–309.
Kataoka K. et al. "Block Copolymer Micelles as Vehicles for Drug Delivery" *Journal of Controlled Release*, vol. 24 (1993) pp. 119–132.
Yokoyama, M. et al. "Characterization and Anticancer Activity of the Micelle–Forming . . . " *Cancer Research* vol. 50 (1990) pp. 1693–1700.
Yokoyama, M. et al. "Toxicity and Antitumor Activity Against Solid Tumors of Micelle–Forming . . . " *Cancer Research* vol. 51 (1991) pp. 3229–3236.
Yokoyama, M. et al. "Preparation of Micelle–Forming Polymer–Drug Conjugates" *Bioconjugate Chem.* vol. 3 (1992) pp. 295–301.
Kwon, G. et al. "Enhanced Tumor Accumulation and Prolonged Circulation Times of Micelle . . . " *Journal of Controlled Release.* vol. 29 (1994) pp. 17–23.
Yokoyama, M. et al. "Influencing Factors on In Vitro Micelle Stability of Adriamycin–Block . . . " *Journal of Controlled Release* vol. 28 (1994) pp. 59–65.

(List continued on next page.)

*Primary Examiner*—Thurman K. Page
*Assistant Examiner*—Blessing Fubara
(74) *Attorney, Agent, or Firm*—Ladas & Parry

(57) ABSTRACT

This invention relates to pharmaceutical formulations of paclitaxel, its derivatives or analogs entrapped into nanoparticles of co-polymeric micelles, a process for preparing the same and the use thereof.

32 Claims, 3 Drawing Sheets

Size of the micellar Nanoparticles with Variation of Temperature

OTHER PUBLICATIONS

Yokoyama, M. et al. "Improved Synthesis of Adriamycin–Conjugated Poly (Ethylene Oxide) . . . " *Journal of Controlled Release*.vol. 32 (1994) pp. 269–277.

Kwon G.S. et al. "Physical Entrapment of Adriamycin in AB Block Copolymer Micelles" *Pharmaceutical Research* vol. 12 No. 2 (1995) pp. 192–195.

Yokoyama, M. et al. "Introduction of Cisplatin into Polymeric Micelle" *Journal of Controlled Release* vol. 39 (1996) pp. 351–356.

La, S.B. et al. "Preparation and Characterization of the Micelle–Forming Polymeric . . . "*Journal of Pharmaceutical Sciences* vol. 85 (1996) pp. 85–90.

Zhang,X et al.Development of Amphiphilic Diblock Copolymers as Interational Journal of Pharmaceutics vol. 132 (1996) pp. 195–206.

Inoue, T. et al. "An AB Block Copolymer of Oligo (Methyl Methacrylate) and Poly . . ." *Journal of Controlled Release* vol. 51 (1998) pp. 221–229.

Kim, S.Y. et al. "Methoxy Poly (Ethylene Glycol) and E–Caprolactone Amphiphilic . . . "*Journal of Controlled Release* vol. 51(1998) pp. 13–22.

Yu, B.G. et al. " Polymeric Micelles for Drug Delivery: Solubilization and Haemolytic . . . " *Journal of Controlled Release* vol. 53 (1998) pp. 131–136.

Kwon, G. et al. "Block Copolymer Micelles for Drug Delivery: Loading and Release of . . . " *Journal of Controlled Release* vol. 48 (1997) pp. 195–201.

Jenkins, P. et al. "Taxol Branches Out" *Chemistry in Britain* (1996) pp. 43–46.

Arbuck, S.G. et al. "Clinical Development of Taxol" *Journal of the National Cancer Institute Monographs* vol. 15 (1993) pp. 11–24.

Long, H.J. "Paclitaxel (Taxol):A Novel Anticancer–Chemotherapeutic Drug" *Mayo Clin. Proc.* vol. 69 (1994) pp. 341–345.

Sharma, A. et al. "Novel Taxol Formulations: Preparation and Characterization . . . " *Pharmaceutical Research* vol. 11 No. 6 (1994) pp. 889–896.

* cited by examiner

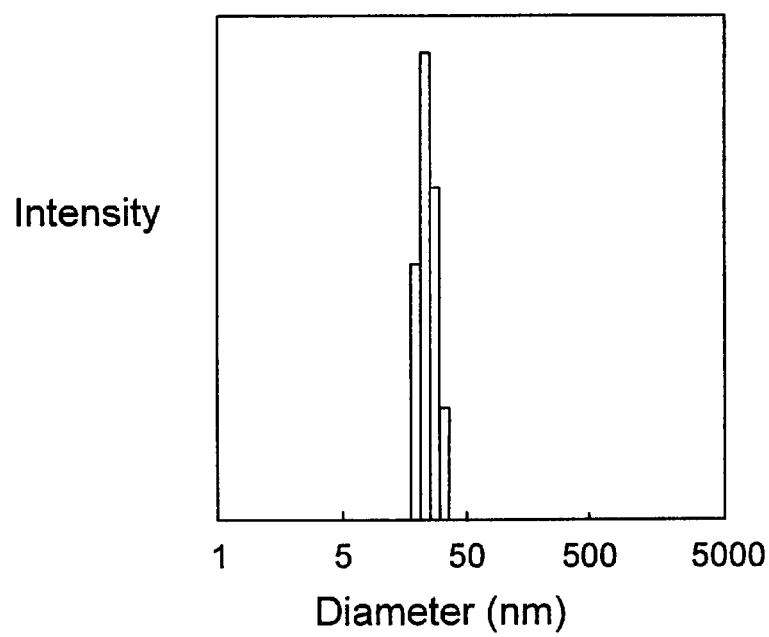
F I G. 1a
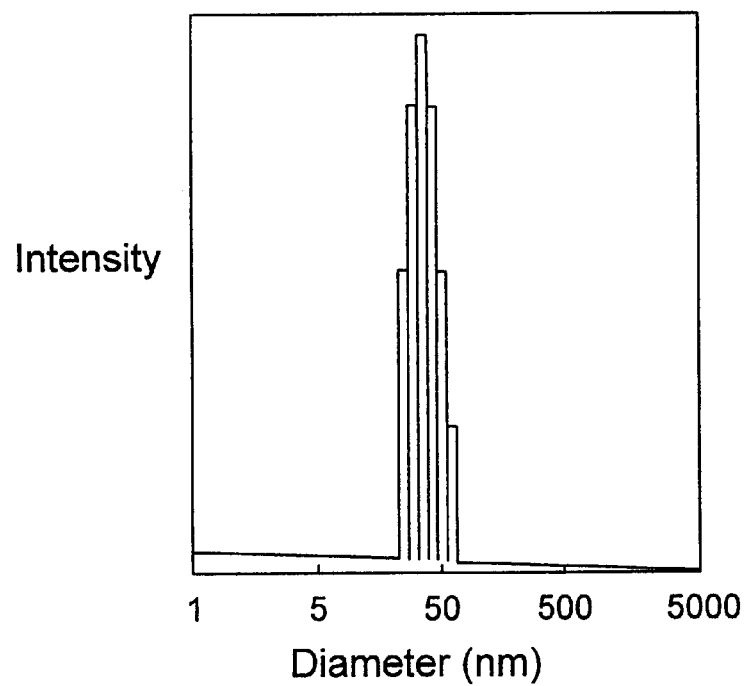
F I G. 1b

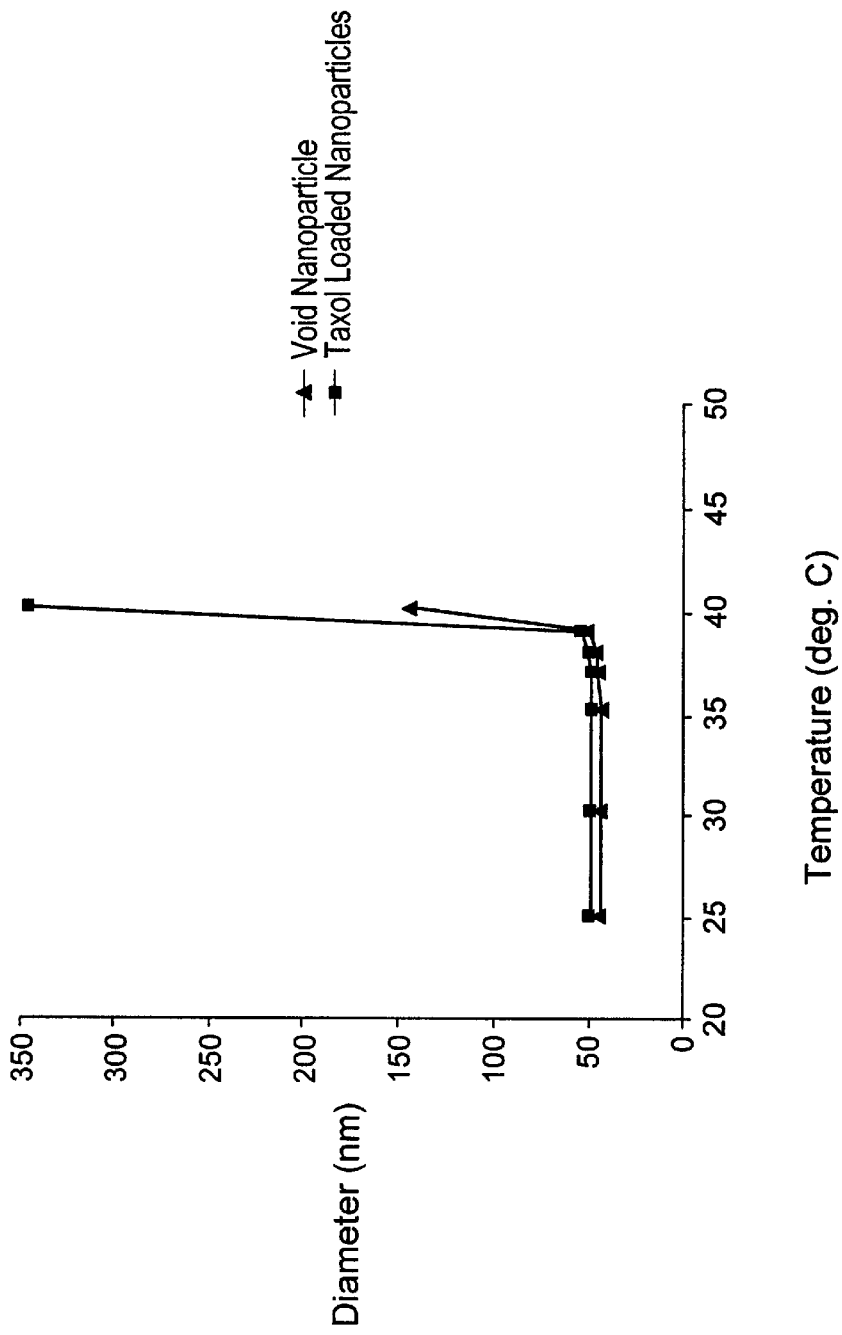

FORMULATIONS OF PACLITAXEL, ITS DERIVATIVES OR ITS ANALOGS ENTRAPPED INTO NANOPARTICLES OF POLYMERIC MICELLES, PROCESS FOR PREPARING SAME AND THE USE THEREOF

This invention relates to pharmaceutical formulations of paclitaxel, its derivatives or analogs entrapped into nanoparticles of co-polymeric micelles, a process for preparing the same and the use thereof.

BACKGROUND OF THE INVENTION

In the last two decades research has focused on the development of efficient systems for site specific delivery of drugs by the use of appropriate carriers, which include liposomes, micelles, polymeric nanoparticles and nanoparticles made of hardened micelles (popularly known as polymeric micelles). The use of liposomes as drug targeting agents is found to be limited mainly due to the problems of low entrapment efficiency, drug instability, rapid drug leakage and poor storage stability. With the aim of overcoming these problems, the use of polymeric nanoparticles and polymeric micelles have been investigated by many scientists during the last two decades.

Nanometer size drug carriers with hydrophilic surfaces are found to evade recognition and uptake by the reticulo-endothelial systems (RES) and thus can circulate in the blood for a long time. Another advantage of these hydrophilic nanoparticles is that, due to their extremely small size, the particles extravasate at the pathological sites such as solid tumors through passive targeting mechanism.

Among the nanometer size hydrophilic drug carriers mentioned above, polymeric micelles, although the least studied, have the potential to deliver hydrophobic drugs. In recent papers and review articles, water-soluble biocompatible polymeric micelles as drug delivery vehicles have been reported.[1-3]

A polymeric micelle usually consists of several hundred block copolymers and has a diameter of about 20 nm-50 nm. There are two spherical co-centric regions of polymeric micelles, a densely packed core of hydrophobic material which is responsible for entrapping the hydrophobic drug and an outer shell made of hydrophilic material for evasion of body's RES which permits circulation in the blood for a longer period of time.

Kataoka and his colleagues [4-15] have extensively studied polymeric micelles as carriers for anticancer and other hydrophobic drugs. They synthesized AB block copolymers of amphiphilic monomers that formed micelles with diameters in a range of several tens of nanometers. In most of these studies the anticancer drug molecules were covalently linked within the micellar core. When the drug was covalently linked within the polymeric micelles, it was difficult to control the cleavage rate of the drug linkage. Some studies have also been reported on the physical entrapment of hydrophobic drugs in these micellar nanoparticles[16-19]. Solubilization of pyrene, doxorubicine and indomethacine into polymeric micelles and their use in vivo studies have been reported in the literature.

Paclitaxel is the first of a new class of anticancer drugs and has been investigated in human trials, in particular for ovarian, breast, colon, non-small cell lung and head and neck cancer[20-23]. Paclitaxel causes stabilization of microtubules and thus interferes with cellular progress through mitosis and arresting cell replication. One problem associated with the use of paclitaxel is its poor solubility in water and in most pharmaceutically acceptable solvents.

Presently, the vehicle of the clinically used formulation comprises 527 mg/ml polyoxyethylated castor oil (Cremophor EL) and 49.7% v/v absolute ethanol. Unfortunately, Cremophor causes hypersensitivity reactions especially in some young children[24]. Moreover, paclitaxel is a toxic drug and therefore, large doses may cause severe toxic reactions[24]. Liposomal formulations may not be very effective because of low entrapment in the hydrophobic layer of liposomes in addition to the other inherent limitations of liposomal formulations[25].

U.S. Pat. No. 5,684,169, describes a method of improving solubility of paclitaxel in water by adding an unbranched cyclodextrin or a branched cyclodextrin thereto at a molar ratio of 1–20 times with respect to paclitaxel. This is totally different from the present invention-preparation of nanoparticles of polymeric micelles and entrapping paclitaxel, its derivatives or analogs into these nanoparticles of polymeric micelles. These nanoparticles of polymeric micelles besides keeping the drug in aqueous solution also help in increasing the circulation time in blood, in vivo.

SUMMARY OF THE INVENTION

The object of this invention is a process for preparing nanoparticles of polymeric micelles which contain paclitaxel, its derivatives or analogs.

A further object of this invention is a process for the preparation of nanoparticles of polymeric micelles constituted of block copolymers that can entrap paclitaxel, its derivatives or analogs to the maximum extent possible.

Another object of this invention is a process for the preparation of nanoparticles of polymeric micelles having intercross-linked polymeric chains so that the release of the entrapped paclitaxel, its derivatives or analogs encapsulated in these micelles can be controlled.

Yet another object of this invention is a process for the preparation of nanoparticles of polymeric micelles loaded with paclitaxel, its derivatives or analogs with polyethyleneglycol chains at the outer surface of the nanoparticle. The polyethyleneglycol chains help the particles to circulate in the blood for a relatively long time.

Still another object of this invention is a process for the preparation of nanoparticles of polymeric micelles loaded with paclitaxel, its derivatives or analogs dispersed in aqueous solution, which are free from unwanted and toxic materials like unreacted monomers.

Another object of this invention is a process for the preparation of nanoparticles of polymeric micelles containing paclitaxel, its derivatives or analogs which can be used for in vivo experiments with a purpose to target maximum amounts of drug to tumors and only negligible amounts to other tissues, which obviates the disadvantages associated with the prior art.

A still further object of this invention is the use of nanoparticles of polymeric micelles loaded with paclitaxel, its derivatives or analogs prepared according to the process of this invention for the treatment of conditions arising out of excessive proliferation of cells.

BRIEF DESCRIPTION OF THE DRAWINGS

FIG. 1(a) shows the diameters of nanoparticles of co-polymeric micelles prepared according to the process of Example II.

FIG. 1(b) shows the diameters of nanoparticles of co-polymeric micelles prepared according to the process of Example III.

FIG. 2 shows the temperature dependent variation of particle size of the nanoparticles prepared by the process of Example II.

DETAILED DESCRIPTION OF THE INVENTION

Figure 3:
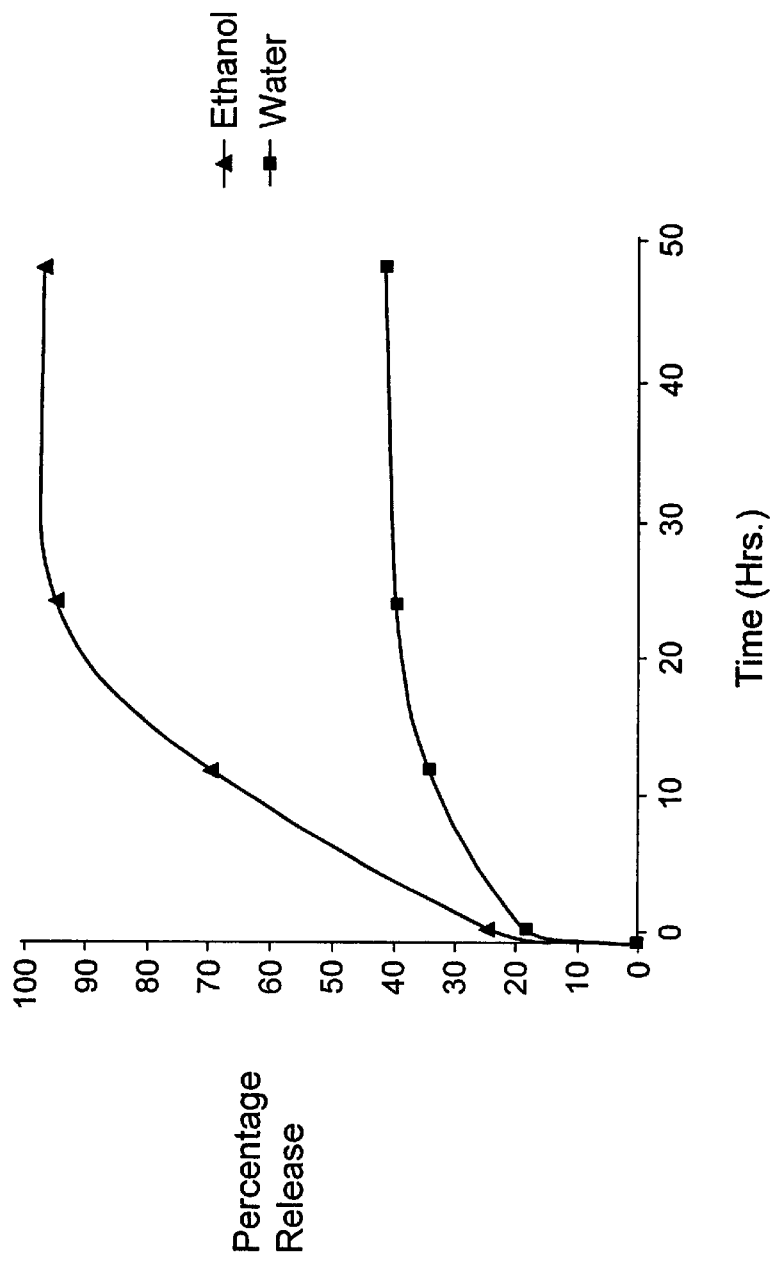
FIG. 3 shows the release of paclitaxel from the nanoparticles of co-polymeric micelles prepared by the process of Example II.

To achieve these objectives, a process for the preparation of pharmaceutical formulations of paclitaxel, its derivatives or analogs entrapped into nanoparticles of co-polymeric micelles is described. Nanoparticles of co-polymeric micelles may be defined as the nanometer size particles of micellar aggregates of amphiphilic polymers.

The process of this invention comprises the steps of:
1. dissolving at least one type of amphiphilic monomer, preferably two types of amphiphic monomers as herein described, in an aqueous medium to obtain micelles,
2. adding an aqueous solution of cross-linking agent, and optionally an activator and initiator as herein described to the micellar solution of the monomers,
3. subjecting the mixture to polymerization in the presence of an inert gas at 20° C. to 80° C., preferably between 30°–40° C., until the polymerization of the micelles is complete,
4. purifying the nanoparticles of the co-polymeric micelles by dialysis to remove toxic monomers and other unreacted materials,
5. dissolving paclitaxel, its derivatives, or analogs in a suitable solvent, generally an alcohol preferably ethanol and adding this solution under stirring to the nanoparticle solution,
6. optionally treating the nanoparticles containing entrapped paclitaxel, its derivatives or analogs with a stabilizer, optionally
7. lypholizing the nanoparticles of co-polymerized micelles containing entrapped paclitaxel, its derivatives or analogs to obtain dry powder, and optionally
8. reconstituting the nanoparticles in suitable medium for human or mammalian administration.

In step 3 of the process described above the completion of polymerization of the monomers is determined by monitoring the depletion of the monomers from the reaction mixture by HPLC.

Dialysis is carried out for 2–4 hours to eliminate unreacted monomers.

Nanoparticles of co-polymeric micelles are formed by the reaction/polymerization of the monomers in the reaction mixture. Random polymer chains are formed and are then cross-linked with each other with the help of a cross-linking agent. The amount of the cross-linking agent affects the amount of cross-linking in the polymer and which in turn affects the compactness of the network formed. The compactness of this network has a direct bearing on the drug entrapment and consequently drug release from these nanoparticles. The more compact the network, the more difficult it is for the drug to be released.

The hydrophobic cores of these nanoparticles of co-polymeric micelles are composed of hydrophobic part of the block copolymers with the hydrophilic part extended outside towards the aqueous medium.

The nanoparticles of co-polymeric micelles prepared by the process of this invention may be used for the treatment of pathological conditions arising out of excessive proliferation of cells such as rheumatoid arthritis or cancer. The formulations can be used to treat ovarian cancer, breast cancer, non-small cell lung cancer, small cell lung cancer, squamous cell cancer of the head and neck and malignant melanomas.

Amphiphilic monomers which form polymers through radical polymerization reaction are preferred. Preferred monomers are vinyl pyrrolidone, acrylic acid, alkyl acrylates having a chain length of $C_3$ to $C_6$ and/or functionalized polyethylene glycol of a molecular weight 2000 to 6000, N-alkyacrylamide having a chain length of $C_3$ to $C_6$, and alkylcyanoacrylate having a chain length of $C_3$ to $C_6$. Two or more amphiphilic monomers are used.

A functionalized polyethyleneglycol is a polyethyleneglycol reacted to another organic compound containing a functional group. A preferred functionalized polyethylene glycol is polyethylene glycol ester of maleic anhydride. Polyethyleneglycol is reacted with maleic anhydride to form polyethylene glycol ester of maleic anhydride. Functionalized polyethyleneglycol may be covalently attached to the polymer chain of the nanoparticles of polymeric micelles with the polyethylene moiety protruding outside on the surface of the nanoparticles.

A preferred combination of amphiphilic monomers is vinylpyrrolidone and N-isopropyl acrylamide in the molar ratio of 90–50:10–50.

Another preferred combination of amphilic monomers is vinylpyrrolidone, N-isopropylacrylamide and monoester of polyethylene glycol maleic anhydride.

The initiators may be peroxide compounds, such as diacyl peroxide compounds such as benzoyl peroxide, diacetyl peroxide or dialkyl peroxides such as tertiary butyl peroxide and tertiary amyl peroxide or perdisulphate or 2, 2'-azo bis isobutyronitrile ALBN).

Activators may be selected from tetramethylethylene diamine (TMED) and ferrous ammonium sulphate.

Any combination of initiator and activator can be used. Two or more initiators can be used. Two or more activators can be used.

The cross-linking agent whenever used is at least a bi-functional vinyl derivative. It can be more than bi-functional (i.e. it can have more than two reactive sites). A bi-functional vinyl derivative that can be used is N,N'methylene bis acrylamide.

The inert gas may be a gas such as nitrogen or argon.

Derivatives and analogs of paclitaxel include the derivative 2-debenzoyl-2-meta-azidobenzoylpaclitaxel and the analog taxotere. Other derivatives and analogs of paclitaxel include but are not limited to:

i. Ring A contracted Paclitaxel Derivatives ii. 10-Deacetyl Paclitaxel iii. 7-Deoxy Paclitaxel iv. Oxetane Ring (ring D) modified Paclitaxel V. 2-Deoxy Paclitaxel vi. 2-Aroyl-2-De Benzoyl Paclitaxel analogues vii. N-Benzoyl Modified Paclitaxel analogues viii. 2,3 cyclohexyl Paclitaxel analogues ix. 4-Deacetyl Paclitaxel analogues x. 7,8-cyclopropane Paclitaxel xi. 7-Fluoropaclitaxel Paclitaxel, its analogues or its derivatives can be added up to a maximum loading of 90% w/w in the nanoparticles of co-polymeric micelles.

Carbohydrates such as sucrose, mannitol, dextrose etc., have a stabilizing effect on the entrapment of drug intside the core of the nanoparticles. This stabilizing effect is further enhanced by the anionic surfactant sodium deoxycholate due to its contribution in enhancement of the hydrophobicity of the core of the micelles. A carbohydrate and sodium deoxycholate together can be used to stabilize the formulation by facilitating the retention of the drug in the aqueous dispersion. Sodium deoxycholate and/or 5–10% dextrose can be used as stabilizers.

In one embodiment, amphiphilic monomers such as vinyl pyrrolidone and N-alkylacrylamide were mixed together in water in molar ratios 90–50:10–50. A cross-linking agent such as N,N' methylene bis acrylamide and an initiator such as ammonium perdisulphate is added in an atmosphere of nitrogen gas to polymerize the monomers. The polymerization reaction was continued at 35° C. for 15 minutes—4 hours under nitrogen atmosphere. Saturated ethanolic solution of paclitaxel, its derivatives or analogs is added according to the desired amount to be entrapped to the maximum extent possible without causing precipitation of the drug. The nanoparticles can then be lyophilized to obtain a dry powder. In accordance with the present invention, the nanoparticles have a size range of a maximum 150 nm diameter, preferably the nanoparticles containing paclitaxel, its derivatives or analogs have a diameter in the range of 30 nm to 60 nm. The diameters become slightly larger when polyethyleneglycol chains are covalently linked on the surface of these nanoparticles.

As the parent micelles are monodispersed, the nanoparticles of co-polymeric micelles entrapping paclitaxel, its derivatives or analogs show monodispersity.

The invention will now be described with reference to the following non-limiting examples:

EXAMPLE I

Preparation of Paclitaxel Loaded Polymeric Nanoparticles Composed of Block Copolymer of Vinylpyrrolidone and N-isopropylacrylamide 10 mg freshly distilled vinylpyrrolidone and 90 mg of N-isopropylacrylamide were added to 10 ml water. To the aqueous solution 28 µl of N,N' methylene bis acrylamide (MBA) (49 mg/ml) was added and the solution was dearated by bubbling nitrogen gas into it for half an hour. 20 µl of TMED and 30 µl of aqueous ammonium perdisulphate (20% w/v) are added and bubbling of nitrogen gas is continued for the entire polymerization reaction time of 24 hours. Polymerization was carried out at 35° C. in a water bath. After polymerization is complete the solution was dialysed for 2–4 hours to remove monomers and other unreacted materials. To the dialysed solution, 5%, alcoholic solution of paclitaxel (20 mg/ml) was added up to the extent required for the desired entrapment. The paclitaxel loaded nanoparticles of co-polymeric micelles were lyophilized to obtain a dry powder.

EXAMPLE II

Preparation of Paclitaxel Loaded Nanoparticles of Polymeric Micelles Composed of Block Copolymer of Vinylpyrrolidone and N-isopropylacrylamide 10 mg freshly distilled vinylpyrrolidone and 90 mg of N-isopropylacrylamide were added in 10 ml water. To the aqueous solution 28 µl of N,N'-methylene bis acrylamide (MBA) (49 mg/ml) was added and the solution was deaerated by bubbling nitrogen gas into it for half an hour. To the micellar solution 20 µl of TMED and 30 µl of aqueous ammonium perdisulphate (20% w/v) and 20 µl of ferrous ammonium sulphate (50%) were added and bubbling of nitrogen gas is continued for the entire polymerization reaction time ranging between 15 minutes and 4 hours. Polymerization was done at 35° C. in a water bath. After polymerization is complete the solution was dialysed for 2–4 hours to remove monomers and other unreacted material. To the dialysed solution, 5% dextrose and sodium deoxycholate were added. To this, an alcoholic solution of paclitaxel (20 mg/ml) was added up to the extent required for desired entrapment.

EXAMPLE III

Preparation of Paclitaxel Loaded Nanoparticles of Polymeric Micelles Composed of Block Copolymer of Vinylpyrrolidone, N-isopropylacrylamide and Monoester of Polyethyleneglycol Maleic Anhydride 30 mg of freshly distilled vinyl pyrrolidone, 60 mg N-isopropylacrylamide and 10 mg of polyethylene glycol (mol. wt. 4000) ester of maleic anhydride are mixed together in 5 ml of water and the nanoparticles of co-polymeric micelles are prepared in the same way as described in examples I and II using initiators and activators. After the completion of polymerization the solution was dialysed for 2–4 hours. 10% dextrose and sodium deoxycholate was added to the dialyzed polymer solution. To this an alcoholic solution of paclitaxel was added to the micelles. The micelles were lyophilized to obtain a dry powder.

EXAMPLE IV

Loading of Paclitaxel into the Nanoparticles of Co-polymeric Micelles and the Shelf Life of Loaded Nanoparticles of Co-polymeric Micelles The paclitaxel loaded nanoparticles of co-polymerc micelles prepared according to example II are found to have maximum loading up to an extent of 90% w/w of the polymeric material. However, with the increased loading of drug the stability of the micelles is reduced and the drug precipates out making the solution turbid.

The shelf life of paclitaxel loaded nanoparticles in water (or aqueous medium)

| Loading % | $1^{st}$ day | $2^{nd}$ day | $3^{rd}$ day | $4^{th}$ day | $5^{th}$ day | $6^{th}$ day | $7^{th}$ day |
|---|---|---|---|---|---|---|---|
| 1% | Clear | Clear | Clear | Clear | Clear | Clear | Clear |
| 2% | Clear | Clear | Clear | Clear | Turbid | — | — |
| 3% | Clear | Turbid | — | — | — | — | — |
| 4% | Turbid* | — | — | — | — | — | — |

Turbid after 3 hours

The shelf life of paclitaxel loaded nanoparticles with polyethyleneglycol on the surface (prepared according to example II) is shown in the following table:

| Loading % | $1^{st}$ day | $2^{nd}$ day | $3^{rd}$ day | $4^{th}$ day | $5^{th}$ day | $6^{th}$ day | $7^{th}$ day |
|---|---|---|---|---|---|---|---|
| 2% | Clear | Clear | Clear | Clear | Clear | Clear | — |
| 4% | Clear | Clear | Clear | Clear | Turbid | — | — |
| 6% | Clear | Turbid | — | — | — | — | — |
| 8% | Turbid* | — | — | — | — | — | — |

Turbid after 2 hours

The shelf life of pacitaxel loaded nanoparticles (prepared according to example III) is shown in the following table:

| Loading % | 1st day | 2nd day | 3rd day | 4th day | 5th day | 6th day | 7th day |
|---|---|---|---|---|---|---|---|
| 4% | Clear | Clear | Clear | Clear | — | — | — |
| 6% | Clear | Clear | Clear | Clear | — | — | — |
| 15% | Clear | Clear | Clear | Clear | — | — | — |
| 20% | Clear | Clear | Clear | Clear | — | — | — |

EXAMPLE V

Size of the loaded nanoparticles.

The size of the paclitaxel loaded nanoparticle prepared according to example I and example II have been determined by light scattering measurements and are shown in the FIGS. 1(a & b).

EXAMPLE VI

The Release behavior:

The paclitaxel loaded nanoparticles prepared according to example II are found to exhibit the release of paclitaxel in aqueous solution very slowly. The quantity of released paclitaxel is determined by HPLC. The results are shown in FIG. 3.

References

1. G. S. Kwon and T. Okano, Adv. Drug Delivery Reviews. 21, 107–116 (1996).
2. G. S. Kwon and K. Kataoka, Adv. Drug Delivery Reviews. 16, 295–309 (1995).
3. S. S. Davis and L. Illum, Biomaterials 9, 111–115 (1988).
4. K. Kataoka, G. S. Kwon, M. Yokoyama, T. Okano and Y. Sakurai, J. Controlled Release 24, 119–132 (1993).
5. M. Yokoyama, S. Inoue, K. Kataoka, N. Yui, T. Okano, Y. Sakurai, Macromol. Chem. 190, 2041–2054 (1989).
6. M. Yokoyama, M. Miyauchi, N. Yamada, T. Okano, Y. Sakurai, K. Kataoka and S. Inoui, Cancer Res. 50, 1693–1700 (1990).
7. M. Yokoyama, T. Okano, Y. Sakurai, H. Ekimoto, C. Shibazki and K. Kataoka, Cancer Res. 51, 3229–3236 (1991).
8. M. Yokoyama, G. S. Kwon, T. Okano, Y. Sakurai, T. Seto and K. Kataoka, Bioconjugate Chem. 3, 295–301 (1992).
9. G. Kwon, S. Suwa, M. Yokoyama, T. Okano, Y. Sakurai and K. Kataoka, J. Controlled Release, 29, 17–23 (1994).
10. M. Yokoyama, G. S. Kwon, T. Okano, Y. Sakurai, M. Naito and K. Kataoka, J. Control Release, 28, 59–65 (1994).
11. M. Yokoyama, T. Okano, Y. Sakurai and K. Kataoka, J. Controlled Release 32, 269–277 (1994).
12. G. S. Kwon, M. Naito, M. Yokoyama, T. Okano, Y. Sakurai, K. Kataoka, Pharm. Res 12, No. 2, 192–195 (1995).
13. M. Yokoyama, T. Okano, Y. Sakurai, S. Suwa and K. Kataoka, J. Controlled Release 39, 351–356 (1996).
14. S. B. La, T. Okano and K. Kataoka, J. Pharma. Sd. 85, 85–90 (1996).
15. X. Zhang, J. K. Jackson, H. M. Burt, Int. J. Pharm. 132,195–206 (1996).
16. T. Inoue, G. Chen, K. Nakamae and A. S. Hoffman, J. Controlled Release, 51, 221–229 (1998).
17. S. Y. Kim, I. G. Shin, Y. M. Lee, C. S. Cho and Y. K. Sung, J. Controlled Release 51, 13–22 (1998).
18. B. G. Yu, T. Okano, K. Kataoka and G. Kwon, J. Controlled Release 53, 131–136 (1998).
19. G. Kwon, M. Naito, M. Yokoyama, T. Okano, Y. Sakurai and K. Kataoka, J. Controlled Release 48, 195–201 (1997).
20. P. Jenkins and N. Lawrence, Chemistry in Britain, 43–46 (1996).
21. S. G. Arbuck, M. C. Christian, J. S. Fisherman, L. A. Cazenave, G. Sarosy, M. Suffness, J. Adams, R. Canetta, K. E. Cole and M. A Fridman, Monogr. Natl. Cancer Inst. 15, 11–24 (1993).
22. H. J. Long, Mayo Clin. Proc. 69, 341–345 (1994).
23. R. Fao, L. Norton, A. D. Seidman, Int. J. Clin. Lab. Res. 24, 6–14 (1994).
24. R. B. Weiss, R. C. Donehower, P. H. Wiemik, T. Ohnuma, R. J. Grallka, D. L. Trump, J. R. Baker, D. A. Vanecho, D. D. Vonhoff and B. Leyland-Jones, J. Clinical Oncology 8,1263–1268 (1990).
25. A. Sharma and R. M. Straubinger, Pharm. Res. 2, 889–896 (1994).

We claim:

1. A process for preparing a pharmaceutical composition of paclitaxel, its derivatives or analogs entrapped into nanoparticles of co-polymeric micelles comprising the steps of:
    a) dissolving at least one type of amphiphilic monomer selected from the group consisting of vinylpyrrolidone, acrylic acid, alkyl acrylates having a chain length of $C_3$ to $C_6$ functionalized polyethylene glycol of a molecular weight of 2000 to 6000, N-alkylacrylamide having a chain length of $C_3$ to $C_6$, and alkylcyanoacrylate having a chain length of $C_3$ to $C_6$, in an aqueous medium to obtain micelles;
    b) polymerizing the micelles by adding an aqueous solution of cross-linking agent;
    c) polymerizing the solution in the presence of an inert gas at 20° C. to 80° C. until the polymerization of micelles is complete;
    d) dialysing the solution of nanoparticles of polymerized micelles to remove toxic monomer and other unreacted materials, and
    e) adding an alcoholic solution of paclitaxel, its derivatives or analogs to the nanoparticles of polymerized micelles.

2. The process of claim 1 wherein an aqueous solution of activator, initiator or a mixture thereof is added in step b).

3. The process of claim 1 wherein a stabilizer is added to the nanoparticles of polymeric micelles containing entrapped paclitaxel, its derivatives or analogs.

4. The process of claim 1 wherein the nanoparticles of polymerized micelles comprising entrapped paclitaxel, its derivatives or analogs are lypholized to obtain a dry powder.

5. The process as claimed in claim 1 wherein the vinylpyrrolidone and N-alkylacrylamide are in a ratio of 90–50:10–50.

6. The process as claimed in claim 1 wherein the inert gas is nitrogen or argon.

7. The process as claimed in claim 1 wherein the polymerized micelles containing paclitaxel have a diameter in the range of 30 nm to 150 nm.

8. The process as claimed in claim 2 wherein the cross-linking agent is a bi-functional vinyl derivative.

9. The process as claimed in claim 8 wherein the bi-functional vinyl derivative is N,N'methylene bis acrylamide.

10. The process as claimed in claim 2 wherein the initiator is a peroxide compound.

11. The process as claimed in claim 10 wherein the peroxide compound is selected from the group consisting of diacyl peroxide, diacetyl peroxide and dialkyl peroxide.

12. The process as claimed in claim 2 wherein the initiator is perdisulphate or 2,2'-azo bis isobutyronitrile ALBN).

13. The process as claimed in claim 2 wherein the activator is tetramethylethylene diamine (TMED), ferrous ammonium sulphate or a mixture thereof.

14. The process as claimed in claim 3 wherein the stabilizer is 5%–10% dextrose.

15. The process as claimed in claim 3 wherein the stabilizer is sodium deoxycholate.

16. The process as claimed in claim 1 wherein the alcoholic solution is a saturated ethanolic solution.

17. The process as claimed in claim 1 wherein the dialysis is carried out for 2–4 hours.

18. The process as claimed in claim 1 wherein the paclitaxel derivatives and analogues are selected from the group consisting of 2-debenzoyl-2-meta-azido-benzoyl, taxotere, ring A contracted paclitaxel derivatives, 10-deacetyl paclitaxel, 7-deoxy paclitaxel, oxetane ring (ring D) modified paclitaxel, 2-deoxy paclitaxel, 2-aroyl-2-debenzoyl paclitaxel analogues, N-benzoyl modified paclitaxel analogues, 2,3 cyclohexyl paclitaxel analogues, 4-deacetyl paclitaxel analogues, 7,8-cyclopropane paclitaxel and 7-fluoropaclitaxel.

19. The process according to claim 1 wherein the polymerization is carried out at a temperature of 30° C.–40° C.

20. Nanoparticles of co-polymeric micelles prepared by the process of claim 1.

21. A method of treating a pathological condition arising out of excessive proliferation of cells comprising administering nanoparticles of co-polymeric micelles of claim 20 to a patient in need thereof.

22. The method according to claim 21 wherein the condition is rheumatoid arthritis.

23. The method according to claim 22 wherein the condition is ovarian cancer, breast cancer, non-small cell lung cancer, small cell lung cancer, squamous cell cancer of the head or neck and malignant melanomas.

24. A process for preparing a composition of paclitaxel, its derivatives or analogs entrapped into nanoparticles of co-polymeric micelles comprising the steps of:
   a) dissolving vinylpyrrolidone and N-alkylacrylamide having a chain length of $C_3$ to $C_6$ in water to obtain micelles;
   b) polymerizing the micelles by adding an aqueous solution of N,N'-methylene bis acrylamide;
   c) polymerizing the solution in nitrogen gas at 35° C. until the polymerization of the micelles is complete;
   d) dialysing the solution of nanoparticles of polymerized micelles to remove toxic monomers and other unreacted materials, and
   e) adding an alcoholic solution of paclitaxel, its derivatives or analogs to the nanoparticles of polymerized micelles.

25. The process according to claim 24 wherein paclitaxel is entrapped into the nanoparticles of co-polymeric micelles.

26. The process according to claim 24 further comprising adding ammonium perdisulphate, tetramethylethylene diamine and ferrous ammonium sulphate to the solution of step b).

27. The process according to claim 24 further comprising adding dextrose and sodium deoxycholate to the solution of step d).

28. The process as claimed in claim 24 wherein the vinylpyrrolidone and N-alkylacrylamide are in a ratio of 90–50:10–50.

29. A process for preparing a composition of paclitaxel, its derivatives or analogs entrapped into nanoparticles of co-polymeric micelles comprising the steps of:
   a) dissolving vinylpyrrolidone and N-alkylacrylamide having a chain length of $C_3$ to $C_6$ and polyethylene glycol ester of maleic anhydride in water to obtain micelles,
   b) polymerizing the micelles by adding an aqueous solution of N,N'-methylene bis acryl amide;
   c) polymerizing the solution in nitrogen gas at 35° C. until the polymerization of the micelles is complete;
   d) dialysing the solution of nanoparticles of polymerized micelles to remove toxic monomers and other unreacted materials, and
   e) adding an alcoholic solution of paclitaxel, its derivatives or analogs to the nanoparticles or polymerized micelles.

30. The process according to claim 29 wherein paclitaxel is entrapped into the nanoparticles of co-polymeric micelles.

31. The process according to claim 29 further comprising adding ammonium perdisulphate, tetramethylethylene diamine and ferrous ammonium sulphate to the solution of step b).

32. The process according to claim 29 further comprising adding dextrose and sodium deoxycholate to the solution of step d).

* * * * *